(12) United States Patent
Eaves

(10) Patent No.: US 8,708,561 B2
(45) Date of Patent: Apr. 29, 2014

(54) MOBILE IMAGING APPARATUS

(75) Inventor: Christopher B. Eaves, Scottsdale, AZ (US)

(73) Assignee: OrthoScan, Inc., Scottsdale, AZ (US)

( * ) Notice: Subject to any disclaimer, the term of this patent is extended or adjusted under 35 U.S.C. 154(b) by 125 days.

(21) Appl. No.: 12/728,130

(22) Filed: Mar. 19, 2010

(65) Prior Publication Data

US 2010/0239073 A1 Sep. 23, 2010

Related U.S. Application Data

(60) Provisional application No. 61/162,152, filed on Mar. 20, 2009, provisional application No. 61/312,104, filed on Mar. 9, 2010.

(51) Int. Cl.
*H05G 1/02* (2006.01)

(52) U.S. Cl.
USPC ............................................... 378/198

(58) Field of Classification Search
USPC .................................. 378/193, 196, 197, 198
See application file for complete search history.

(56) References Cited

U.S. PATENT DOCUMENTS

| | | | | |
|---|---|---|---|---|
| 6,113,265 A | * | 9/2000 | Babler | 378/197 |
| 6,203,196 B1 | * | 3/2001 | Meyer et al. | 378/197 |
| 7,530,739 B2 | * | 5/2009 | Lurz et al. | 378/198 |
| 7,597,473 B2 | * | 10/2009 | Graumann et al. | 378/197 |
| 7,607,832 B2 | * | 10/2009 | Jensen et al. | 378/197 |
| 2004/0254456 A1 | | 12/2004 | Ritter | |
| 2005/0163279 A1 | | 7/2005 | Mitschke et al. | |
| 2005/0234327 A1 | | 10/2005 | Saracen et al. | |
| 2008/0103388 A1 | | 5/2008 | Maschke et al. | |

* cited by examiner

*Primary Examiner* — Jurie Yun
(74) *Attorney, Agent, or Firm* — Knobbe, Martens, Olson & Bear LLC

(57) ABSTRACT

In an exemplary embodiment, an imaging apparatus comprises an arm assembly coupled to an imaging arm. The arm assembly includes a shoulder joint, an elbow joint, and an articulation assembly. The shoulder joint is configured to travel a vertical distance in a substantially linear fashion and provide rotational movement. The imaging arm comprises a first end and a second end. As such, the imaging apparatus is configured to provide radial motion along a path equal to the length of the arm assembly and the imaging arm along the vertical distance and the horizontal distance of the shoulder joint. The imaging apparatus may also comprise a movable cabinet, a monitor, and a control, with the arm assembly coupled to the movable cabinet. Furthermore, the imaging arm may comprise an x-ray source and a sensor, with the monitor displaying data detected by the sensor.

12 Claims, 8 Drawing Sheets

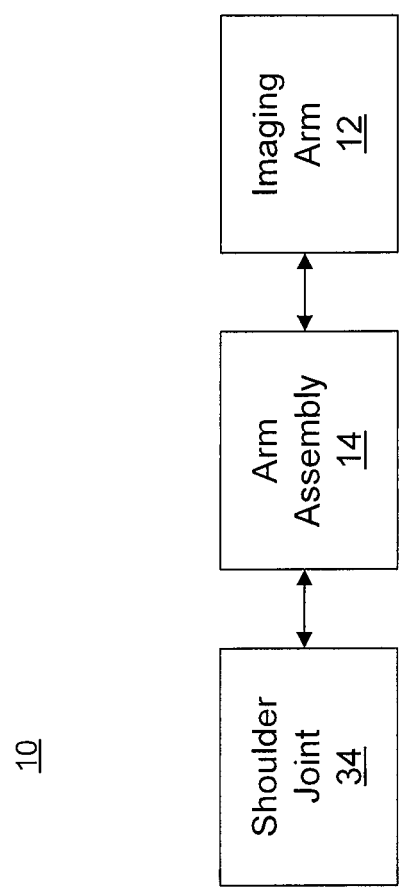

MOBILE IMAGING APPARATUS

CROSS REFERENCE TO RELATED APPLICATION

This application claims priority to U.S. Ser. No. 61/162,152, entitled "MINIATURE C-ARM IMAGING APPARATUS", filed on Mar. 20, 2009, and claims priority to U.S. Ser. No. 61/312,104, entitled "MINIATURE IMAGING APPARATUS", filed on Mar. 9, 2010, the entire disclosures of which are incorporated herein by reference.

FIELD OF THE INVENTION

The present invention generally relates to imaging systems, and, more particularly, to fluoroscopic radiographic imaging systems utilizing a miniature imaging apparatus.

BACKGROUND OF THE INVENTION

Fluoroscopic radiographic imaging systems provide non-invasive means of imaging bone and tissue. Fluoroscopy is the term that describes the process of obtaining multiple radiographic images at regular intervals and displaying them in sequence to create a video image of the anatomy being examined.

A conventional mini imaging apparatus, such as, for example, a mini "C-arm" imaging apparatus may comprise a C-arm assembly, an arm assembly, and a cabinet. The range of motion of the C-arm assembly and the arm assembly controls the operator's ability to position the C-arm assembly relative to the patient. Limitations in the displacement of the C-arm assembly can inhibit the operator's ability to image the patient in various operational and clinical scenarios.

The arc depth of a mini C-arm controls the operator's ability to access patient anatomy during a fluoroscopic examination, whether surgical or clinical. The C-arm movement is typically made of circular arcs to connect an x-ray source to an image intensifier at the prescribed distance, which limits the arc depth.

Accordingly, it is desirable to have a C-arm with a greater arc depth as well as a greater vertical range of motion.

SUMMARY OF THE INVENTION

In accordance with various exemplary embodiments, an imaging system comprises a mechanism configured to provide vertical and rotational motion to an imaging arm.

In an exemplary embodiment, an imaging apparatus comprises an arm assembly coupled to an imaging arm. The arm assembly comprises a shoulder joint, an elbow joint, and an articulation assembly. The shoulder joint is configured to travel a vertical distance and provide rotational movement. The imaging arm comprises a first end and a second end. As such, the imaging apparatus is configured to provide radial motion along a path equal to the length of the arm assembly and the imaging arm along the vertical distance and the horizontal distance of the shoulder joint.

In an exemplary embodiment, an imaging apparatus comprises a movable cabinet, an arm assembly, an imaging arm assembly, a monitor, and a control. The arm assembly is coupled to the movable cabinet. The arm assembly also comprises a coupling configured to provide vertical movement and rotational movement. The imaging arm assembly is coupled to the arm assembly. The imaging arm also comprises an x-ray source and a sensor. The monitor is coupled to the movable cabinet and is in electronic communication with said sensor, such that the monitor is configured to display data detected by the sensor. Finally, the control is coupled to the movable cabinet and is in electronic communication with the x-ray source and is configured to operate said x-ray source.

BRIEF DESCRIPTION OF THE DRAWING FIGURES

A more complete understanding of the present invention may be derived by referring to the detailed description and claims when considered in connection with the Figures, where like reference numbers refer to similar elements throughout the Figures, and:

FIG. 1A is a block diagram describing an imaging apparatus in accordance with an exemplary embodiment;

DETAILED DESCRIPTION OF THE INVENTION

The following description is of exemplary embodiments of the invention only, and is not intended to limit the scope, applicability, or configuration of the invention in any way. Rather, the following description is intended to provide a convenient illustration for implementing various embodiments. As will become apparent, various changes may be made in the function and arrangement of the elements described in these embodiments without departing from the scope of the invention as set forth in the appended claims.

The ability to position imaging components relative to a patient can provide a convenience, a clinical advantage, and a safety advantage in that an imaging device can be made to accommodate the patient's limited mobility. As an example, when imaging a load bearing knee view in a clinical environment, the patient may be required to stand on the damaged or sore knee if the imaging assembly cannot be lowered to capture the required image while the patient is in a more comfortable position. Additionally, the patient may also have to stand on a stool or series of steps that places the patient and physician at increased risk of falling during the examination or stressing the injured anatomy further during the examination.

Thus, an increased vertical range in motion of the imaging assembly allows for imaging a patient in a variety of positions. Such imaging positions may include a shoulder of a standing patient in a clinical environment, or in a surgical environment, a shoulder view of a patient in a beach chair, as well as, knee views of a patient on an elevated table. An increase in arc depth allows an operator of the imaging apparatus to more easily access patient anatomy during examinations. Increasing the maximum range of height and the arc depth allows for maximum versatility of the imaging system, greater accommodation of patient anatomy, and variety in patient positioning.

Figure 1B:
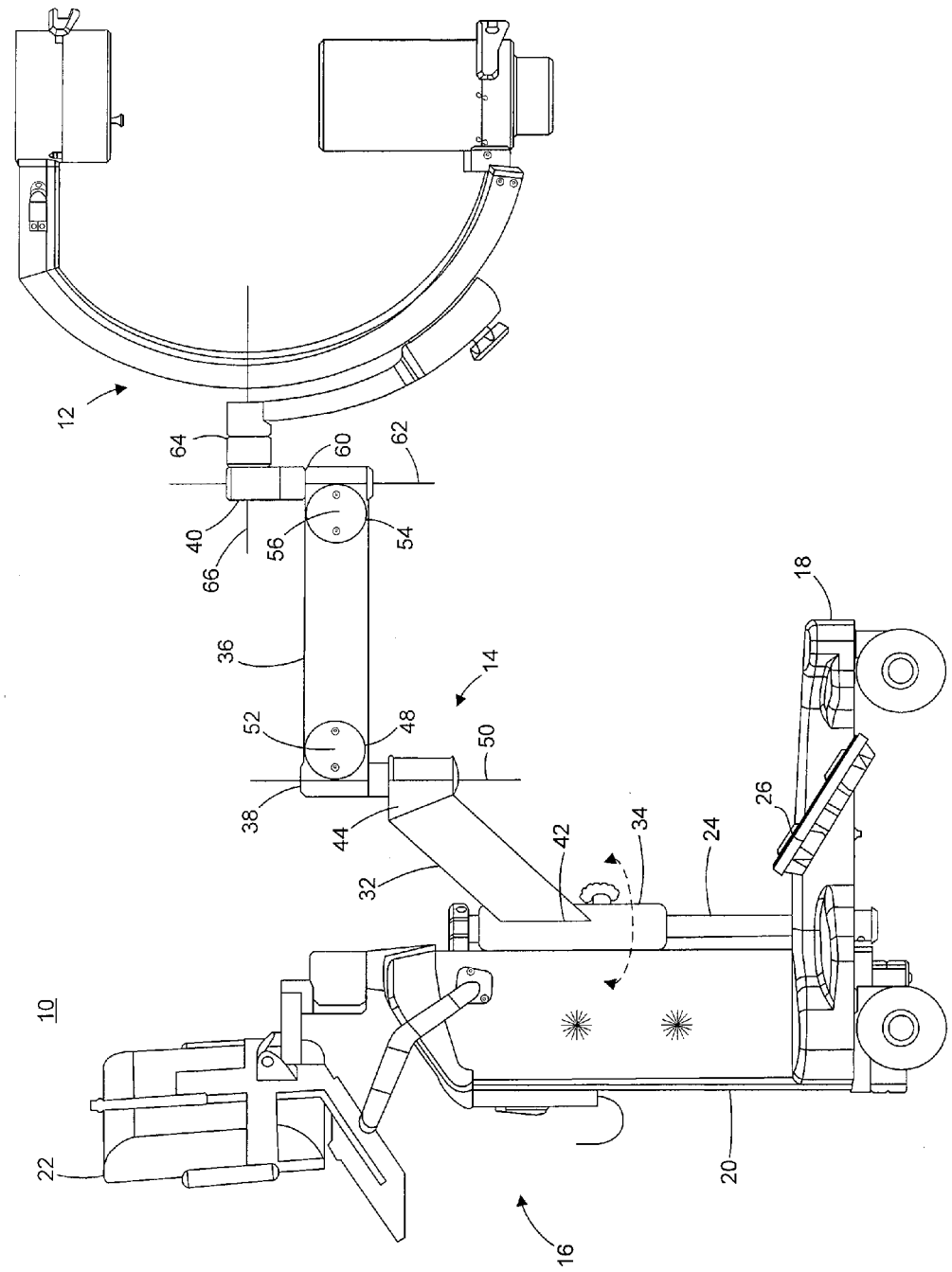
FIG. 1B illustrates an imaging apparatus in accordance with an exemplary embodiment.

In an exemplary embodiment and with reference to FIG. 1A, a mini imaging apparatus 10 is provided. Mini imaging apparatus 10 generally comprises an imaging arm assembly 12, an arm assembly 14, a shoulder joint 34, and a cabinet 16. In an exemplary embodiment, arm assembly 14 is operatively coupled to shoulder joint 34 and imaging arm assembly 12. Imaging arm assembly 12 is configured to support an x-ray source and an x-ray sensor and may comprise one or more supports a body, and one or more rotation mechanisms. Arm assembly 14 is configured to provide horizontal and vertical rotational movement and support imaging arm assembly. Further, arm assembly 14 may comprise one or more sections and joints. Shoulder joint 34 is also coupled to cabinet 16. Shoulder joint 34 is configured to provide vertical and rotational movement of arm assembly 14 with respect to cabinet 16. In an exemplary embodiment illustrated in FIG. 1B, Cabinet 16 includes movable base 18, body portion 20, and at least one monitor 22. In another exemplary embodiment, body portion 20 contains a vertically oriented rod 24.

In an embodiment, cabinet 16 and the electrical subsystems contained therein can be operated by a footswitch control 26, a series of controls located on the outer housing of the x-ray source and keyboard associated therewith. The electrical subsystems are contained within body portion 20 (not shown). An image receptor, such as for example an image intensifier and/or a flat panel detector, receives photons from an x-ray source, by any method or system now known or hereinafter devised. The image receptor converts the x-ray to a manipulable electrical signal that is transmitted to an image processing unit (not shown). The image processing unit may be any hardware and/or software system, now know or hereinafter devised, configured to receive an electrical signal and convert the signal into an image. In an exemplary embodiment, the image processing unit interprets the electrical signals from the image receptor and is able to produce a high-resolution moving image and display the moving image on monitor 22. The image processing unit can be configured to manipulate the image by: removing noise from the image; reducing motion-blur through the averaging multiple frames; rotating the image clockwise or counterclockwise; and or increasing or decreasing image brightness and contrast. The image processing unit can be configured to provide automatic control to x-ray source. The image processing unit can be configured to record the post-processed image to a printer, directly to remote workstation(s) or storage server(s) via industry standard electronic communications protocols, or via an externally connected solid state media device.

In an exemplary embodiment, the image processing unit may be coupled to a network. The image processing unit may also be configured to electrically communicate via an analog or digital signal to provide data to a diagnostic medical information broker system. The diagnostic medical information broker system may be in electronic communication with a patient electronic medical record or electronic health record (collectively "EMR"). As such, the diagnostic medical information broker system provides for, among other things, the relaying of diagnostic medical information and/or patient information between a medical diagnostic modality, including for example mini imaging apparatus 10 and an EMR system. For more details related to an exemplary system and method, see, for example, the system disclosed in U.S. Ser. No. 61/239,001 filed on Sep. 1, 2009 entitled "Diagnostic Medical Information Broker System", which is hereby incorporated by reference in its entirety.

In an exemplary embodiment and with continued reference to FIG. 1B, arm assembly 14 allows imaging arm assembly 12 to reach virtually any point in space within a radius equal to the length of arm assembly 14 and the length of imaging arm assembly 12. When coupled together arm assembly 14 and imaging arm assembly 12 provide for an azimuth of substantially 360 degrees of motion with respect to cabinet 16. Further, the coupling of arm assembly 14 to cabinet 16 provides for an elevation adjustment (e.g. vertical displacement along the shaft of the coupling of arm assembly 14) with respect to cabinet 16 along the length of arm assembly 14.

In an exemplary embodiment, arm assembly 14 may comprise one or more segments, such as for example first arm 32 and second arm 36. Further, arm assembly 14 can include, a shoulder joint 34, an elbow joint 38 and an articulation assembly 40. First arm 32 includes a first end 42 and a second end 44. First end 42 is coupled to cabinet 16 at shoulder joint 34. Second arm 36 is coupled to second end 44 at elbow joint 38. Second arm 36 is also coupled to articulation assembly 40.

In an exemplary embodiment, shoulder joint 34 may be any mechanism configured to provide vertical movement and rotational movement. Shoulder joint 34 may be coupled to any suitable vertical displacement mechanism, including for example, a rod, a gear and track assembly, a manual, hydraulic, or pneumatic lift assembly, and the like. In an exemplary embodiment, shoulder joint 34 is slidably coupled with rod 24 along the length of rod 24, thereby providing movement in a vertical direction along the axis of rod 24. Further, shoulder joint 34 is rotatably coupled with a rod 24 along the axis of rod 24, thereby providing rotational movement of first arm 32 about rod 24. The coupling of first arm 32 to rod 24 provides rotational movement as well as vertical movement of first arm 32, and thus, movement of arm assembly 14 with respect to cabinet 16.

In an exemplary embodiment, vertical adjustment of arm assembly 14 with respect to cabinet 16 may be performed by a manual vertical adjustment mechanism 44, which causes shoulder joint 34 to move vertically on rod 24. In an exemplary embodiment, vertical adjustment mechanism 44 may comprise, for example, a telescoping sleeve, a motorized worm gear, a worm gear with manual crank, a gas spring assisted piston in shaft, a die spring assisted piston in shaft, a linear actuator, a servomotor, a linear rack and hand cranked pinion, a linear rack and motorized pinion, or various combinations of the foregoing mechanisms and the like. It should be understood that any suitable vertical adjustment mechanism now known or hereinafter devised may be used.

Figure 4:
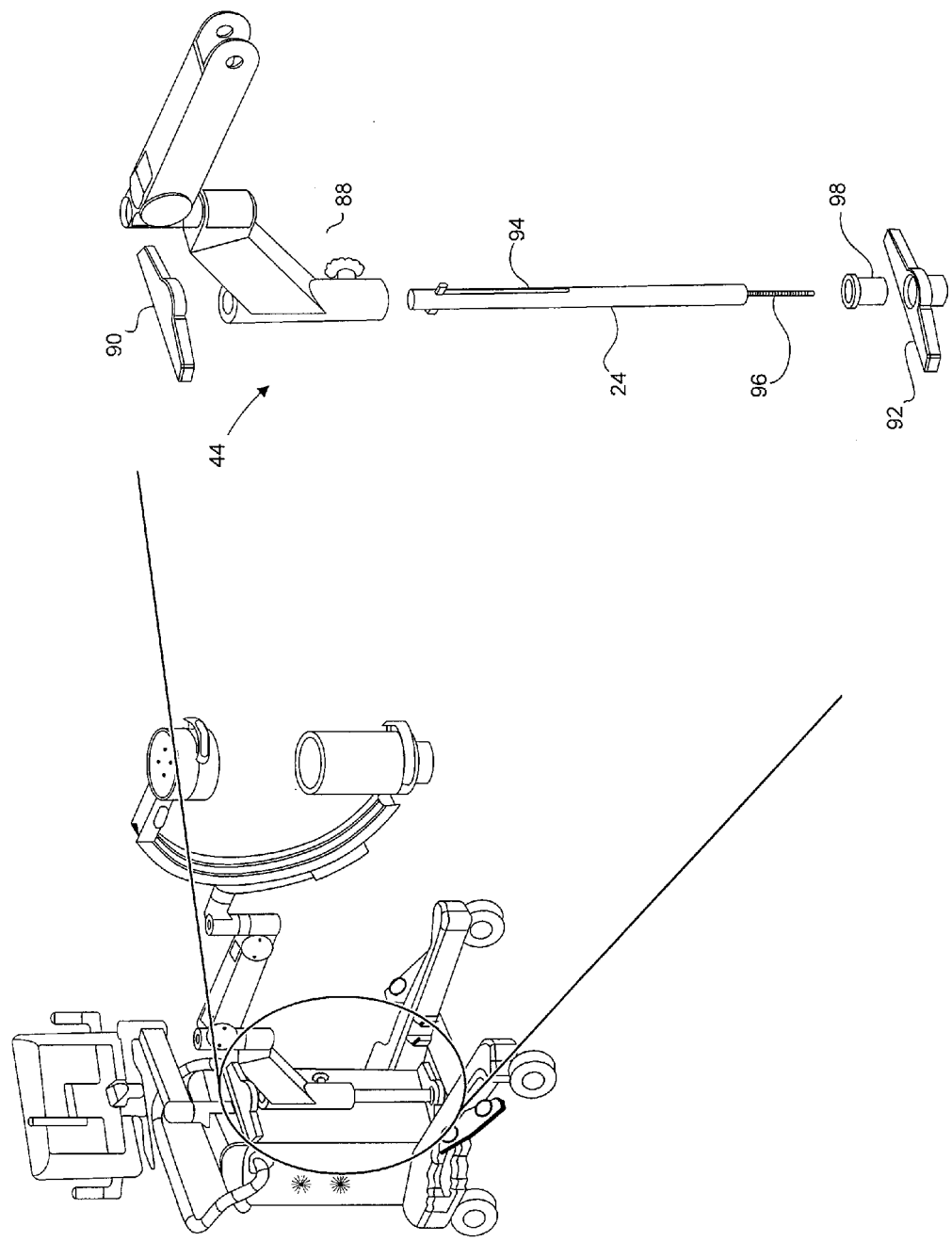
FIG. 4 illustrates an exploded view of a shoulder joint in accordance with an exemplary embodiment.

In an exemplary embodiment and with reference to FIG. 4, vertical adjustment mechanism 44 comprises rod 24, and vertical locking mechanism 88. Vertical adjustment mechanism 44 may be an suitable mechanism for lifting arm assembly 14 in a vertical direction, including for example, a pneumatic mechanism, a hydraulic mechanism, a manual mechanism, an electric mechanism, and the like. Vertical locking mechanism 88 may be any device suitable for locking vertical adjustment mechanism in place, including for example, a spring and detent assembly, a compression assembly, a threaded locking assembly, a pin assembly, and the like. In an exemplary embodiment, rod 24 is coupled to cabinet 16 by a pair of mounting blocks 90, 92. Furthermore, rod 24 may comprise a slot shaft 94 and a gas spring shaft 96. In this embodiment, the lower portion of rod 24 is received in a collar 98, which is, in turn received in mounting block 92. As vertical locking mechanism 88 is unlocked, shoulder joint 34 moves vertically on rod 24, thereby providing a height adjustment of arm assembly 14 with respect to cabinet 16.

Figure 2:
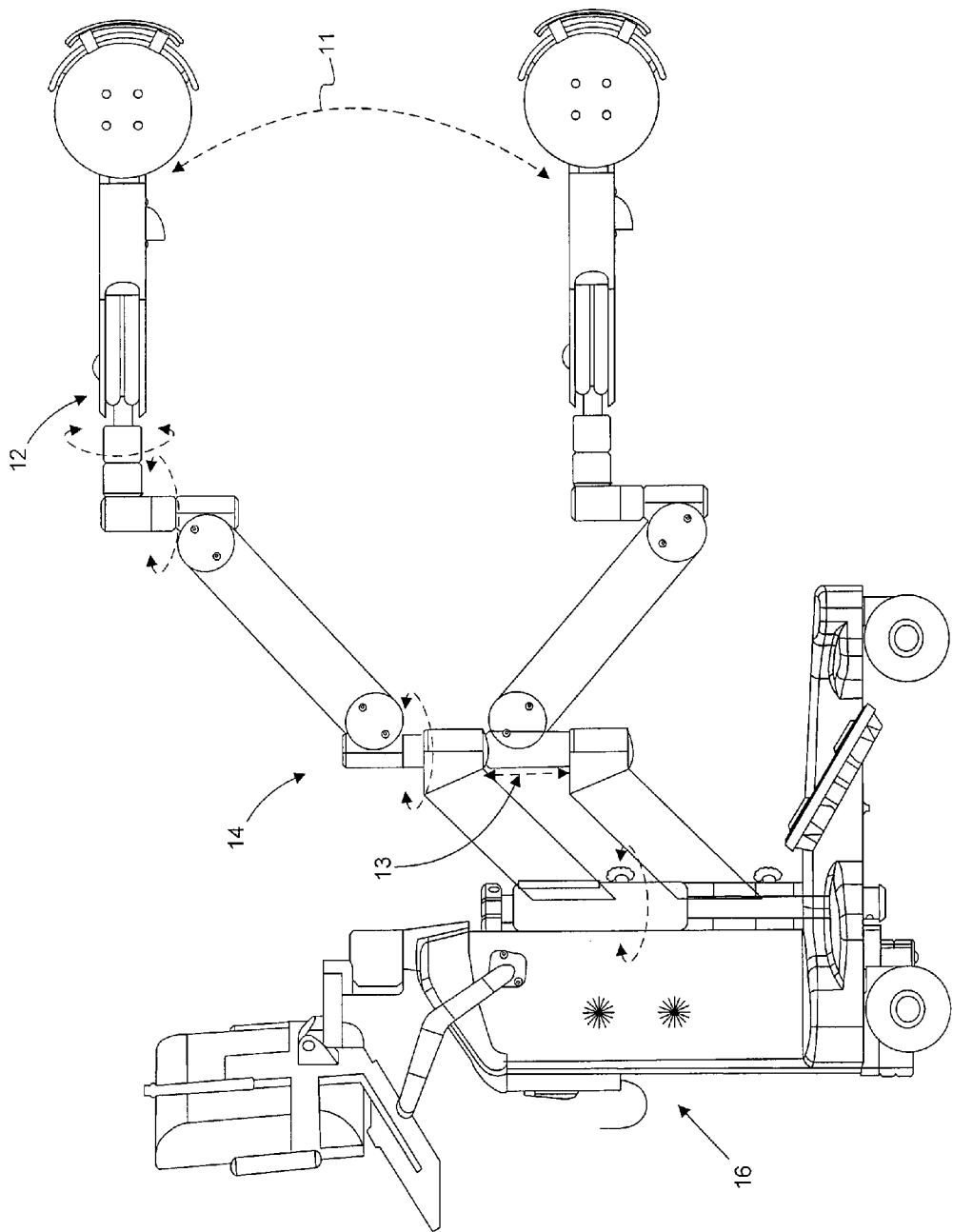
FIG. 2 illustrates the range of vertical motion of an imaging apparatus in accordance with an exemplary embodiment.

Thus, by providing a height adjustment where arm assembly 14 is coupled to cabinet 16, a greater overall range of motion may be obtained, as shown in FIG. 2. This height adjustment adds a range of motion that was previously only attainable by increasing the length of the flex arm height adjustment (second arm 36), or making the overall arm assembly longer to achieve greater radial motion. The increased height range provided by the height adjustment is shown in FIG. 2 at reference numeral 13. With the addition of the height adjustable shoulder geometry, arm assembly 14 can be repositioned relative to cabinet 16 in addition to the vertical range of motion provided by arm assembly 14 alone. As such, an overall increase in vertical range is provided, as shown in FIG. 2 at reference numeral 11, without lengthening the components of arm assembly 14 or adding additional counterweight to cabinet 16.

Referring again to FIG. 1B and in an exemplary embodiment, second end 44 of first arm 32 can be coupled with a first end 48 of second arm 36 at elbow joint 38. Elbow joint 38 provides rotational and pivotal movement between first arm 32 and second arm 36. Elbow joint 38 rotatably couples first arm 32 to second arm 36 along a vertical axis 50, thereby providing rotational movement of second arm 36 with respect to first arm 32 and first arm 32 with respect to second arm 36. Further, elbow joint 38 rotatably couples second arm 36 to first arm 32. Rotational connection 52 allows second arm 36 to rotate with respect to first arm 32 about elbow joint 38 and, thus allows imaging arm assembly 12 to be moved vertically.

In an exemplary embodiment, a second end 54 of second arm 36 couples imaging arm assembly 12 to arm assembly 14 at articulation assembly 40. As such, articulation assembly 40 provides a rotational connection 56 along a horizontal axis 58, a rotational connection 60 about a vertical axis 62, and a rotation connection 64 about a horizontal axis 66. Articulation assembly 40 provides for counter-balanced, rotational, orbital, and pivotal movement of imaging arm assembly 12.

In various embodiments, mini imaging apparatus 10 may comprise any suitable x-ray capture technology. In an exemplary embodiment, mini imaging apparatus 10 comprises an image intensifier. The image intensifier may be configured to amplify diagnostic x-rays to create an output image of an anatomy, such as for example a hand, a knee, and the like. Similarly, mini imaging apparatus 10 may comprise a flat panel detector. The flat panel detector may be any sensor for detecting x-rays and capturing a diagnostic image, now known or hereinafter devised. The flat panel detector may be of any suitable type, including amorphous silicon detectors, amorphous selenium detectors, and plasma based detectors. In an exemplary embodiment, the flat panel detector is configured capture x-ray emitted from an x-ray source, which are converted to a digital image(s) or digital video. In an exemplary embodiment, the image intensifier or flat panel detector are employed in mini-imaging systems to provide lower doses of radiation to a patient.

Figure 3A:
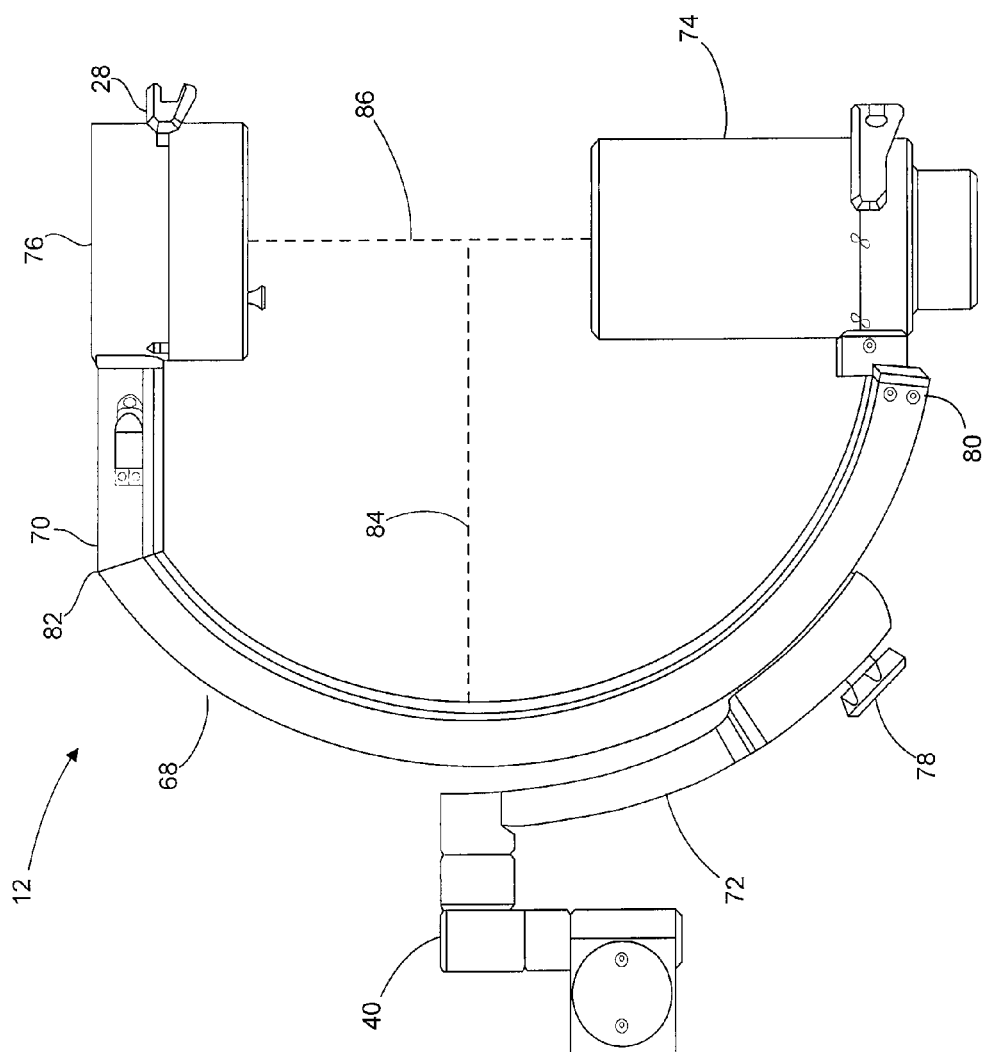
FIG. 3A illustrates a C-arm assembly in accordance with an exemplary embodiment.

With reference to FIG. 3A, an exemplary embodiment of imaging arm assembly 12 of a mini C-arm is illustrated. In an exemplary embodiment, imaging arm assembly 12 may include an arm channel 68, a neck 70, image intensifier 74, and an x-ray source 76. Arm channel 68 may be a rigid track contained within a body that is curved along the arc of a circle. Imaging arm assembly 12 may be coupled with articulation assembly 40 by an arm mount 72. Arm mount 72 may include an adjustment mechanism 78 that moves within arm channel 68 to allow orbital movement and/or rotational of imaging arm assembly 12 with respect to articulation assembly 40. X-ray source 76 and image intensifier 74 may be mounted at opposed locations on arm channel 68, such that x-ray source 76 and image intensifier 74 face each other. Image intensifier 74 is mounted to a lower portion 80 of arm channel 68. Neck 70 is coupled with an upper portion 82 of arm channel 68. Neck 70 is coupled to x-ray source 76.

In an exemplary embodiment, image intensifier 74 is oriented on arm channel 68 such that an arc depth 84 and a source to intensifier distance 86 (SID 86) are created. Arc depth 84 is measured from the center of the image intensifier 74 to the back of the C-channel. SID 86 is measured from the image intensifier 74 and/or the flat panel detector 75 to x-ray source 76.

Figure 3B:
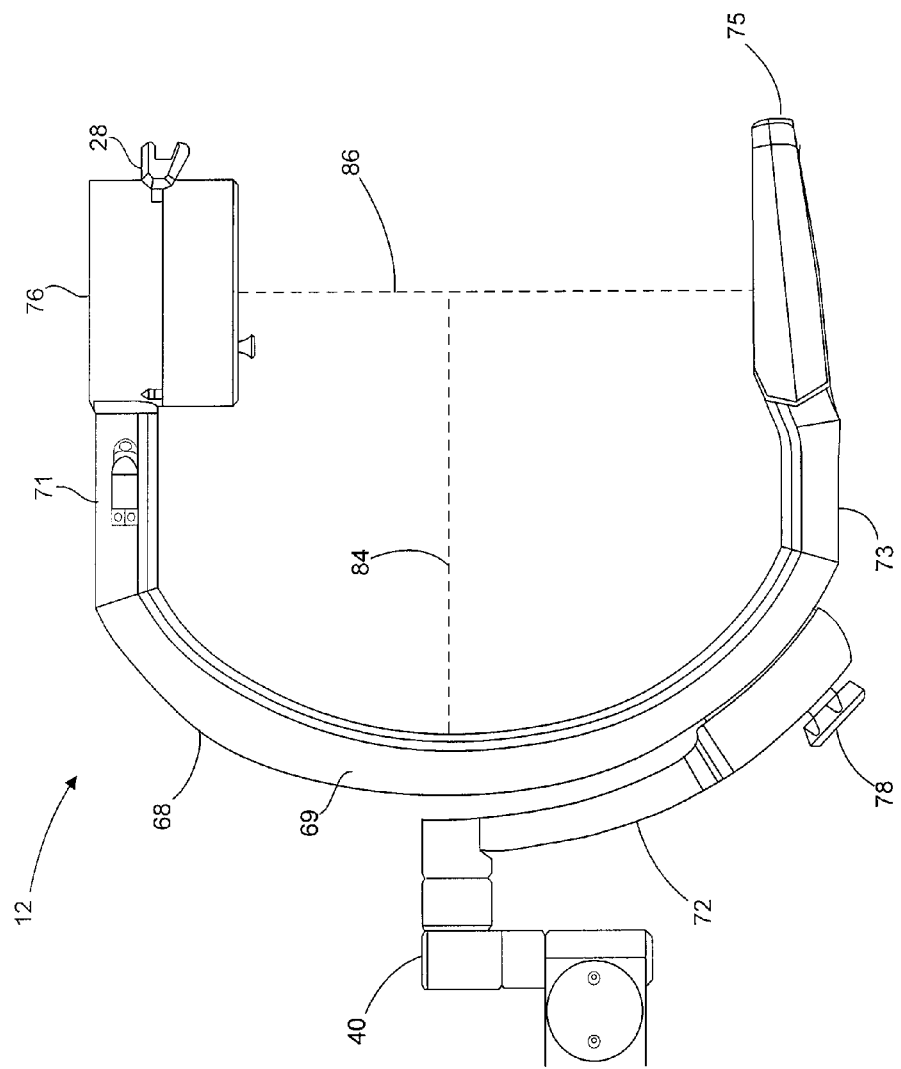
FIG. 3B illustrates a U-arm assembly in accordance with an exemplary embodiment.

In an exemplary embodiment and with reference to FIG. 3B, imaging arm assembly 12 may be configured as a U-arm. Imaging arm assembly 12 may comprise a main body 69, a first support 71, a second support 73, a flat panel detector 75 and an x-ray source 76. As discussed above, main body 69 may be configured to couple to arm mount 72, thereby providing orbital movement of imaging arm assembly 12. First support 71 and second support 73 may be coupled to main body 69 as an assembly and/or integrally formed with main body 69 as a single piece. Furthermore, x-ray source 76 may be removably coupled to first support 71. Similarly, flat panel detector 75 may be removably coupled to the second support 73.

In an exemplary embodiment, main body 69 has a curved and/or semi-circular shape. When coupled to main body 69, first support 71 and second support 73 may be substantially parallel to one another. As such, this configuration has a "U" shape. The arc of main body 69 provides for the substantially parallel configuration between first support 71 and second support 73. Where flat panel detector 75 is employed, the "U" shaped geometry can be effectively employed to limit the overall package size of imaging arm assembly 12. The decrease in the overall package size is accomplished by taking advantage of the low profile of flat panel detector 75. The "U" shaped geometry also provides for an arc depth 84 similar to that of an imaging system employing an image intensifier as shown in FIG. 3A, while having a smaller overall package.

In an exemplary embodiment, the "U" shaped geometry also provides for exposure of flat panel detector 75 to x-ray source 76. As such, the diagnostic surface of flat panel detector 75 may be substantially parallel with the emitting face of x-ray source 76. Further, the diagnostic surface of flat panel detector 75 may be inline with x-ray source 76, such that substantially the entire diagnostic surface of flat panel detector 75 is exposed to the emissions of x-ray source 76.

Additionally, arc depth 84 of imaging arm assembly 12 controls the operator's ability to access patient anatomy during a fluoroscopic examination, whether surgical or clinical. For example, in a surgical environment during a hand case the operator will position imaging arm assembly 12 around a special table called an "arm-board." The arm board is used to support the patient's upper extremity anatomy. As the operator is limited by sterile surgical barriers as to the directions of approach to position imaging arm assembly 12, greater arc depth 84 allows a larger range of imaging area without repositioning the patient or various operating room apparatus. Greater arc depth 84 also allows greater space in which the surgeon can work during an examination in which the fluoroscope is present. This will allow greater maneuverability for tools and surgical or clinical techniques with imaging arm assembly 12 positioned in the examination space.

Furthermore, arc depth 84 has been limited in traditional mini C-arm designs to a size compatible with the FDA requirement for a mini C-arm source to intensifier distance of no greater than 45 cm, as prescribed by Federal Regulation 21 CFR §1020.32(g)(2) (2005). As the C-channels have typically been circular arcs to connect the source to image intensifier 74 at the prescribed distance, the arc depth has been limited as well. The addition of neck 70 to a traditional C-channel allows for a greater arc depth while retaining the FDA specified x-ray source 76 to image intensifier 74 distance. Similarly, employing the "U" shaped geometry with first support 71 and second support 73, illustrated in FIG. 3B allows for a greater arc depth while retaining the FDA specified x-ray source 76 to flat panel detector 75 distance and providing for a smaller overall package.

In exemplary operation the images are captured as x-ray photons and are projected toward the image intensifier and/or flat panel detector. The x-ray photons are converted to an array of electrical signals, which are in turn processed and displayed as either a single radiographic image, or in sequence as a video stream. In an exemplary embodiment, the video signal is broadcast to the monitor in as close to real time as possible. When a user is operating a system in this video mode, it is referred to as "live fluoroscopic imaging" or "fluoroscopy." Upon the completion of fluoroscopy, a still capture of the last single radiographic image displayed is retained and displayed until the next exposure or series of exposure begins. This is referred to as Last Image Hold or "LIH."

Figure 5A:
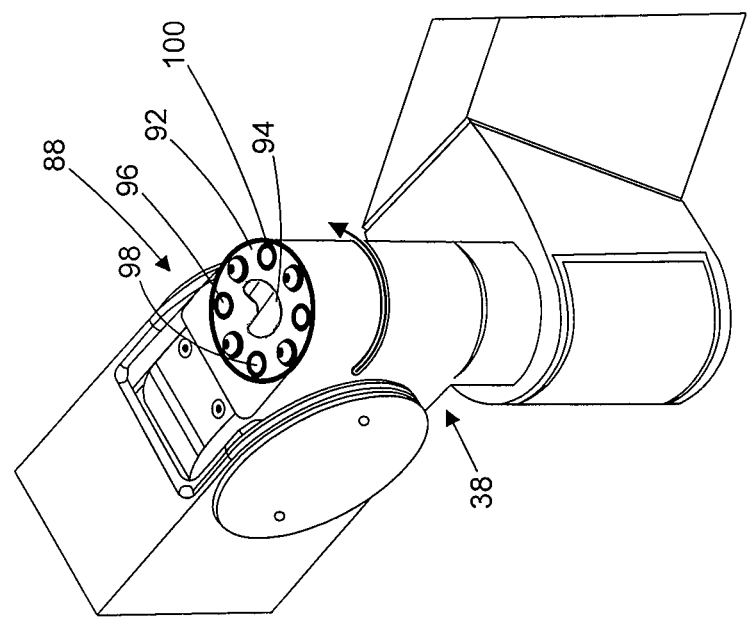
FIGS. 5A and 5B illustrate a pair of soft stops in accordance with an exemplary embodiment.
Figure 5B:
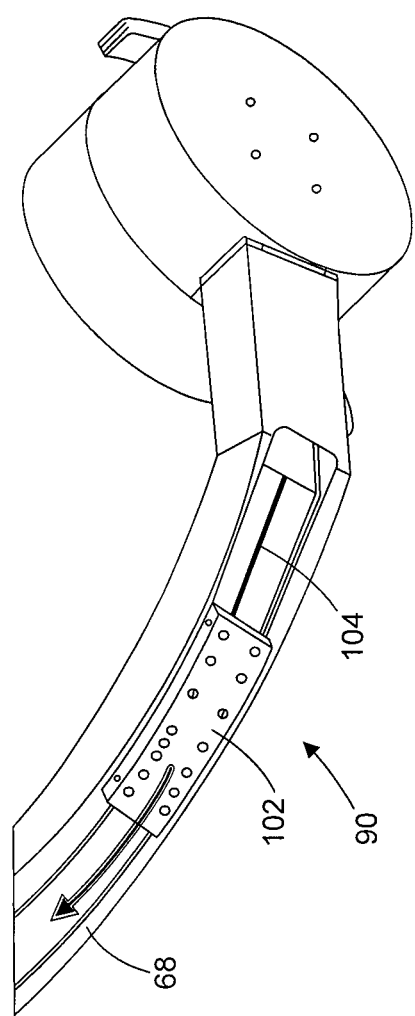

To govern movement between imaging arm assembly 12 and arm assembly 14, stopping devices can be used, for example, referring now to FIGS. 5A and 5B and in accordance with an exemplary embodiment, the stopping devices can comprise a pair of soft stops 88, 90 configured to govern movement of imaging arm assembly 12 and arm assembly 14. Soft stop 88 is included on elbow joint 38 and articulation assembly 40. In an exemplary embodiment, soft stop 88 includes an elbow block stop 92, an elbow shaft 94, and at least one rotation bumper 96 having a peg 98 and bumper stops 100. Furthermore, elbow shaft 94 and rotation bumpers 96 are received in elbow block stop 92.

In an exemplary embodiment, soft stop 90 includes an articulation block 102 and a bumper stop 104. Articulation block 102 is received in a groove on arm channel 68. Moreover, arm mount 72 is coupled with articulation block 102 thereby providing orbital movement of imaging arm assembly 12 with respect to articulation assembly 40.

The lateral motion of arm assembly 14 and imaging arm assembly 12 relative to cabinet 16 is referred to by the industry term "wig-wag." This lateral motion is controlled in range to prevent mechanical instability of mini imaging apparatus 10. When moving a standard C-arm imaging assembly through the lateral range of motion relative to the cabinet, the motions are typically stopped abruptly by metal on metal stopping points. With the addition Of bumper stops 100 on a series of pegs 98 within elbow block stop 92 (which control the range of motion) and bumper stop 104 within arm channel 68, the lateral motion is cushioned when bumping up against the end of a range of motion. This limits component wear and tear, and provides the user a softer more pliable stop when reaching the end of a range of motion. The softer stopping is beneficial when imaging arm assembly 12 is potentially close to a patient and/or a sterile field in which precise positioning is essential to the accurate imaging of the patient.

The present invention has been described with reference to various exemplary embodiments. However, many changes, combinations, and modifications may be made to the exemplary embodiments without departing from the scope of the present invention. For example, the various components may be implemented in alternate ways. These alternatives can be suitably selected depending upon the particular application or in consideration of any number of factors associated with the operation of the system.

When a phrase similar to "at least one of A, B, or C" or "at least one of A, B, and C" is used in the claims, Applicants intend the phrase to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

What is claimed is:

1. An imaging apparatus comprising: a movable base; an arm assembly coupled to said movable base, said arm assembly comprising;
   a shoulder joint;
   a first arm coupled to said shoulder joint, wherein said shoulder joint is configured to provide vertical movement and rotational movement;
   a second arm coupled to said first arm at an elbow joint; and
   an imaging arm coupled to said second arm at an articulation assembly, wherein said imaging arm comprises a first generally linear segment and a second generally linear segment operably connected to an arcuate segment, the first generally linear segment extending generally parallel to the second generally linear segment, wherein the first generally linear segment, second generally linear segment, and arcuate segment substantially form a U-shape, wherein an arc depth of the U-shape comprises an arc depth greater than an arc depth of a circle having a radius equal to the radius of the arcuate segment, wherein said imaging arm further comprises an x-ray source coupled to an end of the first generally linear segment, and an x-ray sensor coupled to an end of the second generally linear segment, wherein the first generally linear segment, the second generally linear segment, the x-ray source, and the x-ray sensor are permanently fixed with respect to the arcuate segment.

2. The imaging apparatus of claim 1, wherein said imaging arm further comprises a support coupled to said articulation assembly, the arcuate segment having a first end, a second end, and a channel between said first end and said second end, wherein the channel is set into an outer surface of the arcuate segment to form at least a single, continuous channel between the first end and the second end, wherein the support coupled to the articulation assembly is configured to connect to the arcuate segment at least in part by way of the channel.

3. The imaging apparatus of claim 2, wherein said support further comprises a movement mechanism coupled to said arcuate segment.

4. The imaging apparatus of claim 3, wherein said arcuate segment is configured to slide along said movement mechanism.

5. The imaging apparatus of claim 1, further comprising:
   an operator input; and a display configured to display outputs from said x-ray sensor.

6. The imaging apparatus of claim 1, wherein said x-ray sensor is at least one of an image intensifier and a flat panel detector.

7. The imaging apparatus of claim 1, wherein said imaging apparatus is configured to provide radial motion along a path equal to the length of said arm assembly and said imaging arm along a vertical path and a rotational path.

8. The imaging apparatus of claim 7, wherein said shoulder joint is configured to provide at least a portion of said vertical path.

9. An imaging apparatus comprising:
   an arm assembly, said arm assembly comprising a shoulder joint, an elbow joint, and an articulation assembly,
   wherein said shoulder joint is configured to travel a vertical distance and provide rotational movement; and an imaging arm coupled to said arm assembly,
   wherein said imaging arm comprises a first end and a second end, wherein said imaging arm comprises a first generally linear segment and a second generally linear segment operably connected to an arcuate segment between the first end and the second end, the first generally linear segment extending generally parallel to the second generally linear segment, wherein the first generally linear segment, second generally linear segment, and arcuate segment substantially form a U-shape, wherein an arc depth of the U-shape comprises an arc depth greater than an arc depth of a circle having a radius equal to the radius of the arcuate segment, wherein said imaging arm further comprises an x-ray source coupled to an end of the first generally linear segment, and an x-ray sensor coupled to an end of the second generally linear segment, wherein the first generally linear segment, the second generally linear segment, the x-ray source, and the x-ray sensor are permanently fixed with respect to the arcuate segment; and wherein said imaging apparatus is configured to provide radial motion along a path equal to the length of said arm assembly and said imaging arm along said vertical distance of said shoulder joint.

10. The imaging apparatus of claim 9, wherein said imaging arm comprises a channel between said first end and second end of said imaging arm and wherein said imaging arm is configured to rotate along said channel.

11. The imaging apparatus of claim 9, wherein the x-ray sensor is at least one of an image intensifier and a flat panel detector.

12. An imaging apparatus, comprising:
a movable cabinet;
an arm assembly coupled with said movable cabinet, said arm assembly comprising a coupling configured to provide vertical movement and rotational movement;
an imaging arm assembly coupled with said arm assembly, said imaging arm assembly comprising an x-ray source and a sensor, wherein said imaging arm assembly comprises a first substantially linear support and a second substantially linear support operably connected to an arcuate segment between the first and second supports, wherein the first substantially linear support and second substantially linear support are defined by their outer perimeters and wherein the arcuate segment is defined by its outer radius, wherein the first support is coupled to the x-ray source and the second support is coupled to the sensor, wherein said first and second supports are substantially parallel to each other, wherein the first support, the second support, the x-ray source, and the sensor are permanently fixed with respect to the arcuate segment;
a monitor coupled to said movable cabinet and in electronic communication with said sensor, wherein said monitor is configured to display data detected by said sensor; and
a control coupled to said movable cabinet and in electronic communication with said x-ray source, wherein said control is configured to operate said x-ray source.

\* \* \* \* \*